United States Patent
Patel et al.

(10) Patent No.: US 7,909,848 B2
(45) Date of Patent: *Mar. 22, 2011

(54) TISSUE RETRACTOR AND GUIDE DEVICE

(75) Inventors: Tushar Patel, Potomac, MD (US); Eric D. Kolb, Milton, MA (US); Jonathan Fanger, Fall River, MA (US)

(73) Assignee: DePuy Spine, Inc., Rayaham, MA (US)

( * ) Notice: Subject to any disclaimer, the term of this patent is extended or adjusted under 35 U.S.C. 154(b) by 1251 days.

This patent is subject to a terminal disclaimer.

(21) Appl. No.: 10/777,019

(22) Filed: Feb. 11, 2004

(65) Prior Publication Data

US 2007/0244489 A1    Oct. 18, 2007

Related U.S. Application Data

(63) Continuation-in-part of application No. 10/609,123, filed on Jun. 27, 2003.

(51) Int. Cl.
*A61B 1/32* (2006.01)
*A61B 17/80* (2006.01)

(52) U.S. Cl. .................. 606/201; 606/280

(58) Field of Classification Search .......... 606/61, 606/69–71, 96, 104, 246, 279, 280; 600/201, 600/205, 210, 219, 221, 235
See application file for complete search history.

(56) References Cited

U.S. PATENT DOCUMENTS

| | | | |
|---|---|---|---|
| 1,920,821 A | 8/1933 | Wassenaar | |
| 2,466,023 A | 4/1949 | Griffin | |
| 2,486,303 A | 10/1949 | Longfellow | |
| 2,494,229 A | 1/1950 | Wollpert et al. | |
| 2,695,688 A | 11/1954 | Wollpert et al. | |
| 2,756,742 A * | 7/1956 | Barton | 600/205 |
| 3,244,170 A | 4/1966 | McElvenny | |
| 3,463,148 A | 8/1969 | Allgower et al. | |
| 3,552,389 A | 1/1971 | Allgower et al. | |
| 3,596,656 A | 8/1971 | Kaute et al. | |
| 3,626,471 A * | 12/1971 | Florin | 600/205 |
| 3,659,595 A | 5/1972 | Haboush | |
| 3,695,259 A | 10/1972 | Yost | |

(Continued)

FOREIGN PATENT DOCUMENTS

DE    4201043    1/1992

(Continued)

OTHER PUBLICATIONS

Product Literature, by SYNTHES Spine, "The Cervical Spine Locking Plate" CSLP, 2000.

(Continued)

*Primary Examiner* — Eduardo C. Robert
*Assistant Examiner* — David Comstock
(74) *Attorney, Agent, or Firm* — Nutter McClennen & Fish LLP

(57) ABSTRACT

A tissue retractor and guide device for use in securing a spinal fixation plate to a spine is provided. In general, the device includes an elongate member having a guide member formed thereon or mated thereto with at least one pathway for receiving a tool. The guide member is adapted to be juxtapositioned on a spinal implant, while the distal portion of the elongate member is effective to retract tissue disposed adjacent to the guide member.

44 Claims, 7 Drawing Sheets

U.S. PATENT DOCUMENTS

| | | |
|---|---|---|
| 3,716,050 A | 2/1973 | Johnston |
| 3,779,240 A | 12/1973 | Kondo et al. |
| 3,824,995 A | 7/1974 | Getscher et al. |
| 3,900,025 A | 8/1975 | Barnes, Jr. |
| RE28,841 E | 6/1976 | Allgower et al. |
| 4,119,092 A | 10/1978 | Gil et al. |
| 4,187,841 A | 2/1980 | Knutson |
| 4,219,015 A | 8/1980 | Steinemann et al. |
| 4,224,699 A | 9/1980 | Weber et al. |
| 4,257,411 A | 3/1981 | Cho |
| 4,388,921 A | 6/1983 | Sutter et al. |
| 4,408,601 A | 10/1983 | Wenk et al. |
| 4,454,876 A | 6/1984 | Mears |
| RE31,628 E | 7/1984 | Allgower et al. |
| 4,493,317 A | 1/1985 | Klaue et al. |
| 4,502,475 A | 3/1985 | Weigle |
| 4,503,848 A | 3/1985 | Caspar et al. |
| 4,513,744 A | 4/1985 | Klaue et al. |
| 4,524,765 A | 6/1985 | de Zbikowski et al. |
| 4,541,424 A | 9/1985 | Grosse et al. |
| 4,651,724 A | 3/1987 | Berentey et al. |
| 4,686,972 A | 8/1987 | Kurland |
| 4,733,657 A | 3/1988 | Kluger |
| 4,744,353 A | 5/1988 | McFarland |
| 4,773,402 A | 9/1988 | Asher et al. |
| 4,800,874 A | 1/1989 | David et al. |
| 4,838,252 A | 6/1989 | Klaue et al. |
| 4,848,327 A | 7/1989 | Perdue |
| 4,887,596 A | 12/1989 | Sherman |
| 4,936,844 A | 6/1990 | Chandler et al. |
| 4,957,495 A | 9/1990 | Kluger |
| 5,002,544 A | 3/1991 | Klaue et al. |
| 5,006,120 A | 4/1991 | Carter |
| 5,041,113 A | 8/1991 | Biedermann et al. |
| 5,041,114 A | 8/1991 | Chapman et al. |
| 5,041,133 A | 8/1991 | Sayano et al. |
| 5,052,373 A | 10/1991 | Michelson |
| 5,053,036 A | 10/1991 | Perren et al. |
| 5,059,194 A | 10/1991 | Michelson |
| 5,067,477 A | 11/1991 | Santangelo |
| 5,088,472 A | 2/1992 | Fakhrai |
| 5,129,899 A | 7/1992 | Small et al. |
| 5,129,903 A | 7/1992 | Luhr et al. |
| 5,147,361 A | 9/1992 | Ojima et al. |
| 5,151,103 A | 9/1992 | Tepic et al. |
| 5,180,381 A | 1/1993 | Aust |
| 5,234,290 A | 8/1993 | Collins |
| 5,275,601 A | 1/1994 | Gogolewski et al. |
| 5,303,694 A | 4/1994 | Mikhail |
| 5,306,278 A | 4/1994 | Dahl et al. |
| 5,318,567 A | 6/1994 | Vichard et al. |
| 5,324,290 A | 6/1994 | Zdeblick et al. |
| 5,324,295 A | 6/1994 | Shapiro |
| 5,336,224 A | 8/1994 | Selman |
| 5,342,295 A | 8/1994 | Imran |
| 5,364,399 A | 11/1994 | Lowery et al. |
| 5,365,921 A | 11/1994 | Bookwalter et al. |
| 5,415,660 A | 5/1995 | Campbell et al. |
| 5,423,826 A | 6/1995 | Coates et al. |
| 5,439,463 A | 8/1995 | Lin |
| 5,501,684 A | 3/1996 | Schlapfer et al. |
| 5,520,690 A | 5/1996 | Errico et al. |
| 5,531,746 A | 7/1996 | Errico et al. |
| 5,531,751 A | 7/1996 | Schultheiss et al. |
| 5,534,027 A | 7/1996 | Hodorek |
| 5,549,612 A | 8/1996 | Yapp et al. |
| 5,558,622 A | 9/1996 | Greenburg |
| 5,578,034 A | 11/1996 | Estes |
| 5,601,553 A | 2/1997 | Trebing et al. |
| 5,603,713 A | 2/1997 | Aust |
| 5,607,426 A | 3/1997 | Ralph et al. |
| 5,607,428 A | 3/1997 | Lin |
| 5,616,142 A | 4/1997 | Yuan et al. |
| 5,616,144 A | 4/1997 | Yapp et al. |
| 5,643,265 A | 7/1997 | Errico et al. |
| 5,651,283 A | 7/1997 | Runciman et al. |
| 5,669,915 A | 9/1997 | Caspar et al. |
| 5,672,177 A | 9/1997 | Seldin |
| 5,676,666 A | 10/1997 | Oxland et al. |
| 5,713,904 A | 2/1998 | Errico et al. |
| 5,735,853 A | 4/1998 | Olerud et al. |
| 5,745,884 A | 4/1998 | Carnegie et al. |
| 5,749,873 A | 5/1998 | Fairley et al. |
| 5,749,884 A | 5/1998 | Benderev et al. |
| 5,755,721 A | 5/1998 | Hearn |
| 5,788,630 A | 8/1998 | Furnish |
| 5,807,396 A | 9/1998 | Raveh |
| 5,827,286 A | 10/1998 | Incavo et al. |
| 5,836,950 A | 11/1998 | Hansson |
| RE36,020 E | 12/1998 | Moore et al. |
| 5,846,193 A | 12/1998 | Wright |
| 5,851,207 A | 12/1998 | Cesarone |
| 5,865,848 A | 2/1999 | Baker |
| 5,876,402 A | 3/1999 | Errico et al. |
| 5,885,286 A | 3/1999 | Sherman et al. |
| 5,888,204 A | 3/1999 | Ralph et al. |
| 5,904,683 A | 5/1999 | Pohndorf et al. |
| 5,931,838 A | 8/1999 | Vito |
| 5,951,558 A | 9/1999 | Fiz et al. |
| 5,954,722 A | 9/1999 | Bono |
| 5,964,762 A | 10/1999 | Biedermann et al. |
| 5,964,763 A | 10/1999 | Incavo et al. |
| 5,967,141 A | 10/1999 | Heinonen et al. |
| 5,967,171 A | 10/1999 | Dwyer, Jr. |
| 5,984,926 A | 11/1999 | Jones |
| 6,006,581 A | 12/1999 | Holmes |
| 6,017,345 A | 1/2000 | Richelsoph |
| 6,030,389 A | 2/2000 | Wagner et al. |
| 6,039,740 A | 3/2000 | Olerud et al. |
| 6,063,090 A | 5/2000 | Schlapfer et al. |
| 6,066,142 A | 5/2000 | Serbousek et al. |
| 6,066,175 A | 5/2000 | Henderson et al. |
| 6,106,527 A | 8/2000 | Wu et al. |
| 6,113,602 A | 9/2000 | Sand |
| 6,117,173 A | 9/2000 | Taddia et al. |
| 6,132,432 A | 10/2000 | Richelsoph |
| 6,139,550 A | 10/2000 | Michelson |
| D433,506 S | 11/2000 | Asfora |
| 6,143,012 A | 11/2000 | Gausepohl et al. |
| 6,152,927 A | 11/2000 | Farris et al. |
| 6,159,244 A | 12/2000 | Suddaby |
| 6,193,721 B1 | 2/2001 | Michelson |
| 6,200,348 B1 | 3/2001 | Biedermann et al. |
| 6,206,828 B1 | 3/2001 | Wright |
| 6,206,881 B1 | 3/2001 | Frigg et al. |
| 6,224,602 B1 | 5/2001 | Hayes |
| 6,227,124 B1 | 5/2001 | Gaydos et al. |
| 6,228,085 B1 | 5/2001 | Theken et al. |
| 6,235,033 B1 | 5/2001 | Brace et al. |
| 6,235,034 B1 | 5/2001 | Bray |
| 6,241,731 B1 | 6/2001 | Fiz et al. |
| 6,258,092 B1 | 7/2001 | Dall et al. |
| 6,258,098 B1 | 7/2001 | Taylor et al. |
| 6,261,291 B1 | 7/2001 | Talaber et al. |
| 6,273,889 B1 | 8/2001 | Richelsoph |
| 6,277,124 B1 | 8/2001 | Haag |
| 6,293,949 B1 | 9/2001 | Justis et al. |
| 6,306,136 B1 | 10/2001 | Baccelli |
| 6,306,139 B1 | 10/2001 | Fuentes et al. |
| 6,309,393 B1 | 10/2001 | Tepic et al. |
| 6,322,562 B1 | 11/2001 | Wolter et al. |
| 6,328,738 B1 | 12/2001 | Suddaby |
| 6,331,179 B1 | 12/2001 | Freid et al. |
| 6,332,887 B1 | 12/2001 | Knox |
| 6,340,363 B1 | 1/2002 | Bolger et al. |
| 6,342,055 B1 | 1/2002 | Eisermann et al. |
| 6,342,056 B1 | 1/2002 | Mac-Thiong et al. |
| 6,342,057 B1 | 1/2002 | Brace et al. |
| 6,379,364 B1 | 4/2002 | Brace |
| 6,402,756 B1 | 6/2002 | Ralph et al. |
| 6,413,259 B1 | 7/2002 | Lyons et al. |
| 6,416,518 B1 | 7/2002 | DeMayo |
| 6,419,678 B1 | 7/2002 | Asfora |
| 6,428,542 B1 | 8/2002 | Michelson |
| 6,441,602 B1 | 8/2002 | Eckhardt et al. |
| 6,447,512 B1 | 9/2002 | Landry et al. |
| 6,454,769 B2 | 9/2002 | Wagner et al. |

| | | |
|---|---|---|
| 6,503,250 B2 | 1/2003 | Paul |
| 6,511,484 B2 | 1/2003 | Torode et al. |
| 6,524,318 B1 | 2/2003 | Longhini et al. |
| 6,527,776 B1 | 3/2003 | Michelson |
| 6,533,786 B1 | 3/2003 | Needham et al. |
| 6,545,769 B2 | 4/2003 | Collard et al. |
| 6,565,571 B1 | 5/2003 | Jackowski |
| 6,575,975 B2 | 6/2003 | Brace et al. |
| 6,585,738 B1 | 7/2003 | Mangione et al. |
| 6,592,586 B1 | 7/2003 | Michelson |
| 6,595,993 B2 | 7/2003 | Donno et al. |
| 6,602,255 B1 | 8/2003 | Campbell et al. |
| 6,602,257 B1 | 8/2003 | Thramann |
| 6,620,163 B1 | 9/2003 | Michelson |
| 6,641,613 B2 | 11/2003 | Sennett |
| 6,652,525 B1 | 11/2003 | Assaker et al. |
| 6,656,181 B2 | 12/2003 | Dixon et al. |
| 6,663,562 B2 * | 12/2003 | Chang .................. 600/219 |
| 6,669,700 B1 | 12/2003 | Farris et al. |
| 6,673,115 B2 | 1/2004 | Resch et al. |
| 6,679,883 B2 | 1/2004 | Hawkes et al. |
| 6,692,503 B2 | 2/2004 | Foley et al. |
| 6,695,846 B2 | 2/2004 | Richelsoph et al. |
| 6,712,818 B1 | 3/2004 | Michelson |
| 6,755,833 B1 | 6/2004 | Paul et al. |
| 6,770,096 B2 | 8/2004 | Bolger et al. |
| 6,793,658 B2 | 9/2004 | LeHuec et al. |
| 6,796,986 B2 | 9/2004 | Duffner |
| 6,913,463 B2 | 7/2005 | Blacklock |
| 6,960,216 B2 | 11/2005 | Kolb et al. |
| 7,011,665 B2 | 3/2006 | Null et al. |
| 7,094,242 B2 | 8/2006 | Ralph et al. |
| 7,147,599 B2 | 12/2006 | Phillips et al. |
| 7,278,997 B1 | 10/2007 | Mueller et al. |
| 7,357,804 B2 | 4/2008 | Binder, Jr. et al. |
| 7,416,553 B2 | 8/2008 | Patel et al. |
| 7,488,327 B2 | 2/2009 | Rathbun et al. |
| 2001/0009971 A1 | 7/2001 | Sherts et al. |
| 2001/0021851 A1 | 9/2001 | Eberlein et al. |
| 2001/0037112 A1 | 11/2001 | Brace et al. |
| 2001/0047172 A1 | 11/2001 | Foley et al. |
| 2002/0022843 A1 | 2/2002 | Michelson |
| 2002/0022847 A1 | 2/2002 | Ray et al. |
| 2002/0045897 A1 | 4/2002 | Dixon et al. |
| 2002/0045898 A1 | 4/2002 | Freid et al. |
| 2002/0049444 A1 | 4/2002 | Knox |
| 2002/0055741 A1 | 5/2002 | Schlapfer et al. |
| 2002/0058939 A1 | 5/2002 | Wagner et al. |
| 2002/0058940 A1 | 5/2002 | Frigg et al. |
| 2002/0082606 A1 | 6/2002 | Suddaby |
| 2002/0143336 A1 | 10/2002 | Hearn |
| 2002/0147450 A1 | 10/2002 | LeHuec et al. |
| 2002/0151899 A1 | 10/2002 | Bailey et al. |
| 2002/0156474 A1 | 10/2002 | Wack et al. |
| 2002/0183754 A1 | 12/2002 | Michelson |
| 2002/0183757 A1 | 12/2002 | Michelson |
| 2002/0188296 A1 | 12/2002 | Michelson |
| 2002/0198533 A1 | 12/2002 | Geisler et al. |
| 2003/0023242 A1 | 1/2003 | Harrington |
| 2003/0040749 A1 | 2/2003 | Grabowski et al. |
| 2003/0045880 A1 | 3/2003 | Michelson |
| 2003/0060828 A1 | 3/2003 | Michelson |
| 2003/0065251 A1 | 4/2003 | Feng et al. |
| 2003/0083658 A1 | 5/2003 | Hawkes et al. |
| 2003/0135213 A1 | 7/2003 | LeHuec et al. |
| 2003/0181912 A1 | 9/2003 | Michelson |
| 2003/0187436 A1 | 10/2003 | Bolger et al. |
| 2003/0187440 A1 | 10/2003 | Richelsoph et al. |
| 2003/0187442 A1 | 10/2003 | Richelsoph et al. |
| 2003/0187454 A1 | 10/2003 | Gill et al. |
| 2003/0208204 A1 | 11/2003 | Bailey et al. |
| 2003/0229348 A1 | 12/2003 | Sevrain |
| 2003/0233098 A1 | 12/2003 | Markworth |
| 2004/0015169 A1 | 1/2004 | Gause |
| 2004/0015174 A1 | 1/2004 | Null |
| 2004/0019353 A1 | 1/2004 | Freid et al. |
| 2004/0034352 A1 | 2/2004 | Needham et al. |
| 2004/0034354 A1 | 2/2004 | Paul |
| 2004/0087951 A1 | 5/2004 | Khalili |
| 2004/0092947 A1 | 5/2004 | Foley |
| 2004/0097935 A1 | 5/2004 | Richelsoph et al. |
| 2004/0133205 A1 | 7/2004 | Thramann et al. |
| 2004/0204710 A1 | 10/2004 | Patel et al. |
| 2004/0204712 A1 | 10/2004 | Kolb et al. |
| 2004/0204716 A1 | 10/2004 | Fanger et al. |
| 2004/0204717 A1 | 10/2004 | Fanger et al. |
| 2004/0210232 A1 | 10/2004 | Patel et al. |
| 2004/0267274 A1 | 12/2004 | Patel et al. |
| 2005/0021040 A1 | 1/2005 | Bertagnoli |

FOREIGN PATENT DOCUMENTS

| | | |
|---|---|---|
| EP | 0897697 | 2/1999 |
| FR | 2827150 | 1/2003 |
| WO | WO-9632071 | 10/1996 |
| WO | WO-0022999 | 4/2000 |
| WO | WO-0064359 | 11/2000 |
| WO | WO-02085226 | 10/2002 |
| WO | WO 03/007826 | 1/2003 |
| WO | WO-03/024344 | 3/2003 |
| WO | 03063714 | 8/2003 |

OTHER PUBLICATIONS

Product Literature, by SYNTHES Spine, *The Cervical Spine Locking Plate* CSLP, 2000.

Cervi-Lok™ Surgical Technique Manual (pp. 1-19), 1995 SPINETECH Inc.®, L1015 Revision B.

* cited by examiner

TISSUE RETRACTOR AND GUIDE DEVICE

CROSS-REFERENCE TO RELATED APPLICATIONS

This application is a continuation-in-part of U.S. patent application Ser. No. 10/609,123, filed on Jun. 27, 2003, entitled "Tissue Retractor and Drill Guide," which is expressly incorporated herein by reference.

FIELD OF THE INVENTION

The present invention relates to devices for assisting in spinal surgery, and more particularly to a tissue retractor and guide device for introducing spinal tools and devices.

BACKGROUND OF THE INVENTION

Advancing age, as well as injury, can lead to changes in the bones, discs, joints, and ligaments of the spine, producing pain from nerve root compression. Under certain circumstances, alleviation of pain can be provided by performing a spinal fusion. This is a procedure that involves joining two or more adjacent vertebrae with a bone fixation device so that they no longer are able to move relative to each other. For a number of known reasons, bone fixation devices are useful for promoting proper healing of injured or damaged vertebral bone segments caused by trauma, tumor growth, or degenerative disc disease. The external fixation devices immobilize the injured bone segments to ensure the proper growth of new osseous tissue between the damaged segments. These types of external bone fixation devices often include internal bracing and instrumentation to stabilize the spinal column to facilitate the efficient healing of the damaged area without deformity or instability, while minimizing any immobilization and post-operative care of the patient.

One such device is a bone fixation plate that is used to immobilize adjacent skeletal parts such as bones. Typically, the fixation plate is a rigid metal or polymeric plate positioned to span bones or bone segments that require immobilization with respect to one another. The plate is fastened to the respective bones, usually with bone screws, so that the plate remains in contact with the bones and fixes them in a desired position. Bone plates can be useful in providing the mechanical support necessary to keep vertebral bodies in proper position and bridge a weakened or diseased area such as when a disc, vertebral body or fragment has been removed.

Such plates have been used to immobilize a variety of bones, including vertebral bodies of the spine. These bone plate systems usually include a rigid bone plate having a plurality of screw openings. The openings are either holes or slots for screw placement. The bone plate is placed against the damaged vertebral bodies and bone screws are used to secure the bone plate to the spine and optionally to a prosthetic implant or bone graft positioned between the adjacent vertebrae. Implantation of the plate, however, can be difficult. Each plate must be properly aligned with the vertebral bodies, and holes for receiving the bone screws must be drilled into the vertebrae at precise angles. It is often necessary to use the bone plate as a drill guide for drilling and tapping the bone in preparation for receiving the bone screws. Such a procedure can be difficult, however, as the surgeon is required to securely and rigidly hold the bone plate against the vertebrae, obtain proper alignment, drill, tap, and finally set the bone screws.

The procedure may be further complicated by the need to retract tissue from the surrounding area. Retraction has traditionally required additional tools and an extra step to pull tissue away from the working area prior to and during the procedure. The use of such additional tools can hinder access to the site and can require a surgeon or an assistant to perform multiple tasks simultaneously. A retractor which is left in place during the procedure can also cause stress to the surrounding tissue and may cause the patient additional discomfort and a prolonged recuperation.

Accordingly, there remains a need for an instrument that can be used to perform multiple tasks during spinal surgery.

SUMMARY OF THE INVENTION

The present invention generally provides a tissue retractor and guide device having an elongate member with a distal portion that is adapted to retract tissue, and a guide member that is coupled to the elongate member and that includes at least one pathway formed therein for receiving a tool. In use, the guide member is adapted to be positioned in relation to a spinal implant, and preferably to be juxtapositioned on a spinal implant such that the pathway is aligned with at least one corresponding bore formed in the spinal implant to guide a tool through the bore.

The guide member can have a variety of configurations, shapes, and sizes, but in general the guide member includes at least one pathway, and more preferably two pathways, formed therein. The pathways can be separate from one another, such that they are defined by lumens extending through a single housing or extending through two separate housings, such as barrels, or alternatively they can be at least partially in communication with one another such that they are formed within a hollow housing. In an exemplary embodiment, the guide member includes front and back opposed sidewalls, opposed lateral sidewalls extending between the front and back sidewalls, and two pathways formed therebetween. The back sidewall of the guide member is preferably coupled to the elongate member.

In another embodiment, the guide member can include at least one cut-out portion formed therein and adapted to provide visual access to a spinal implant coupled thereto. Preferably, a cut-out portion is formed in the front sidewall between the two pathways, and it extends from the proximal end to the distal end of the guide member. As a result of the cut-out portion, the pathways are at least partially in communication with one another.

The guide member of the tissue retractor and guide device can also optionally include one or more alignment features formed thereon and adapted to align the guide member with a spinal implant. In an exemplary embodiment, the alignment feature(s) is in the form of an extension portion that extends distally from the guide member, and that is preferably adapted to rest against a perimeter of a spinal implant to align the guide member with the implant. More preferably, the alignment feature is in the form of first and second tabs that extend distally from a distal-most end of the guide member. Each tab can vary in shape and size, but each tab preferably has a substantially concave inner surface that is adapted to be positioned against a substantially concave outer surface formed on a perimeter of a spinal implant. In another embodiment, the alignment feature can be in the form on an extension portion that extends from the back sidewall of the guide member, or that is formed on and extends distally from the distal portion of the elongate member. Preferably, a distal-most surface of the extension portion is substantially concave to match the contour of a vertebral body.

In another embodiment of the present invention, the tissue retractor and guide device can include at least one mating element formed thereon and adapted to mate with a corresponding mating element formed on a spinal implant. The mating element is preferably formed on a distal end of the guide member, and it can be, for example, a pin, spike, groove, cleat, hole, hook, threaded hole, threaded pin, and combinations thereof. In an exemplary embodiment, the mating element has a shape that is adapted to prevent rotation between the guide member and a spinal implant when the guide member is juxtapositioned on the spinal implant.

In other aspects of the present invention, the guide member can include a first barrel having a lumen extending therethrough, and a second barrel having a lumen extending therethrough. The first and second barrels are preferably positioned at an angle with respect to one another, and more preferably the first and second barrels lie in a plane that is substantially parallel to at least a portion of a front surface of the distal portion of the elongate member. At least one of the first and second barrels of the guide member has an adjustable trajectory such that the barrel can pivot about a point on a longitudinal axis thereof. The barrels can optionally be removably mated to the guide member.

The present invention also provides a tissue retractor and guide kit that includes at least one tissue retractor and guide device that is adapted to couple to a spinal implant. The device has a guide member with opposed front and back sidewalls, opposed lateral sidewalls extending between the front and back sidewalls, and at least one pathway formed therein receiving a tool. An elongate member is coupled to the back sidewall of the guide member and includes a proximal, handle portion, and a distal, tissue-retracting portion.

In one embodiment, the kit includes a cross member that is adapted to removably connect two tissue retractor and guide devices. The cross member can have a variety of configurations, and by way of non-limiting example, it can be in the form of a substantially rectangular housing, or it can be in the form of an elongate rod having opposed ends, each of which are adapted to removably mate to a tissue retractor and guide device.

In another embodiment, the kit includes a spinal fixation plate having a superior portion with at least one bore formed therein for receiving a fixation device effective to mate the superior portion to a first vertebrae, and an inferior portion with at least one bore formed therein for receiving a fixation device effective to mate the inferior portion to a second, adjacent vertebrae. The guide device is adapted to be juxtapositioned on the spinal fixation plate, preferably such that two pathways extending through the guide member align with two adjacent bores formed in at least one of the superior portion and the inferior portion of the spinal fixation plate.

DETAILED DESCRIPTION OF THE INVENTION

In general, the present invention provides a tissue retractor and guide device that is useful during spinal surgery to retract tissue, as well as to facilitate implantation of a spinal implant, such as a spinal fixation plate. The device includes an elongate member having a proximal, handle portion, and a distal portion that is adapted to retract tissue disposed adjacent thereto. A guide member is coupled to the distal portion of the elongate member, and it includes at least one pathway, and more preferably two pathways, extending therethrough for receiving a tool. In use, the distal portion of the elongate member is adapted to retract tissue disposed adjacent to the guide member, and the guide member is adapted to be juxtapositioned on a spinal implant such that the pathway is aligned with a corresponding bore formed in the spinal implant. A tool can then be passed along the pathway and through the corresponding bore in the implant.

The tissue retractor and guide device of the present invention is particularly advantageous in that it combines the functions of a tissue retractor and a guide devices, thereby allowing a surgeon to retract tissue surrounding a surgical site while simultaneously using the guide member to introduce tools to facilitate implantation of a spinal implant. The device further allows a relatively small incision to be used to access the surgical site since it eliminates the need for additional tissue retraction tools. The device is also advantageous in that it allows a surgeon to selectively retract tissue only as needed, rather than retracting tissue during the entire procedure, which can cause stress on the tissue.

A person skilled in the art will appreciate that, while the device is described for use in connection with a spinal fixation plate, the tissue retractor and guide device can be used with a variety of implants for a variety of medical procedures. Moreover, the term "tool" as used herein is intended to include a variety of devices and/or implants.

Figure 1:
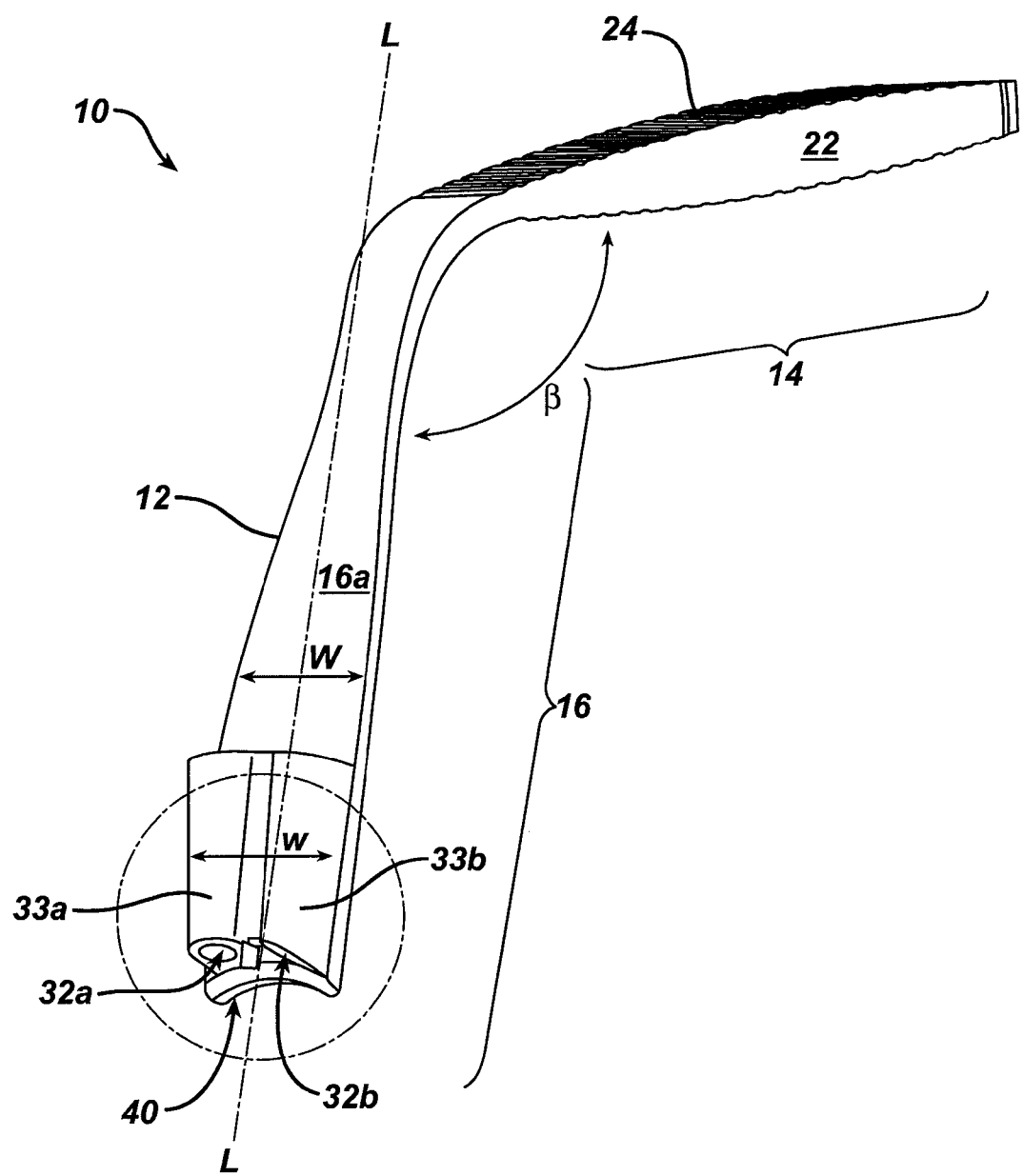
FIG. 1 is a side perspective view of a tissue retractor and guide device according to one embodiment of the present invention.

FIGS. 1-4 illustrate one embodiment of a tissue retractor and guide device 10 in accordance with the present invention. As shown, the device 10 includes an elongate member 12 having a proximal, handle portion 14, and a distal portion 16 that is coupled to a guide device 30. The elongate member 12 can have a variety of configurations, shapes and sizes, but it should be effective to retract tissue adjacent to the guide member 30 during use of the device 10. In an exemplary embodiment, the proximal portion 14 is adapted to extend out of a patient's body, and the distal portion 16 is effective to retract tissue. The proximal and distal portions 14, 16 can be fixedly attached to, removably mated to, or integrally formed with one another, but preferably the proximal portion 14 is disposed at an angle β with respect to the distal portion 16, as shown in FIG. 1, to facilitate visual access to the surgical site. While the angle β between the proximal and distal portions 14, 16 can vary, in an exemplary embodiment, the angle β is in the range of about 110° to 160°, and more preferably it is in the range of about 125° to 145°. Moreover, while only a single bend is shown between the proximal and distal portions 14, 16, a person skilled in the art will appreciate that the elongate member 12 can include two or more bends to facilitate visual access to the surgical site and/or to facilitate positioning of the device 10 in the patient's body. The proximal portion 14 can also optionally be adjustably movable with respect to the distal portion 16 to allow the surgeon to adjust the angle and/or position of the proximal portion 14 with respect to the distal portion 16.

The handle 22 on the proximal portion 14 of elongate member 12 can also have a variety of configurations, shapes, and sizes. In an exemplary embodiment, the handle 22 includes a gripping surface 24, such as a knurled surface, ridges, or grooves, to facilitate grasping of the device 10. In an alternative embodiment, or in addition to the handle 22, the proximal portion 14 of the elongate member 12 can include a clamp member (not shown) formed thereon or mated thereto that is effective to mate the device 10 to a surgical retractor, such as, for example a Bookwalter retractor. Alternatively, the surgical retractor can contain a post or surface for attaching to a Bookwalter having a clamp. A person skilled in the art will appreciate that a variety of clamp members and/or other mating techniques can be used to mate the device 10 to a retractor or other type of support member.

The distal portion 16 of the elongate member 12 can also have a variety of shapes and sizes, and it can mate to, or be integrally formed with, any portion of the guide member 30. In an exemplary embodiment, the distal portion 16 has a generally elongate shape and includes front and back surfaces 16a, 16b that define a width W. While the width W can vary, the width W is preferably sufficient to retract tissue around the guide member 30 to provide access to the guide member 30 and the surgical site. In an exemplary embodiment, at least a portion of the distal portion 16 has a width W that is equal to or greater than a width w of the guide member 30. The width W of the distal portion can also optionally increase in a proximal-to-distal direction. A person skilled in the art will appreciate that a back sidewall of the guide member 30 can form part of the distal portion 16 of the elongate member 12, and that the guide member 30 can be effective to retract tissue disposed therearound.

Figure 2:
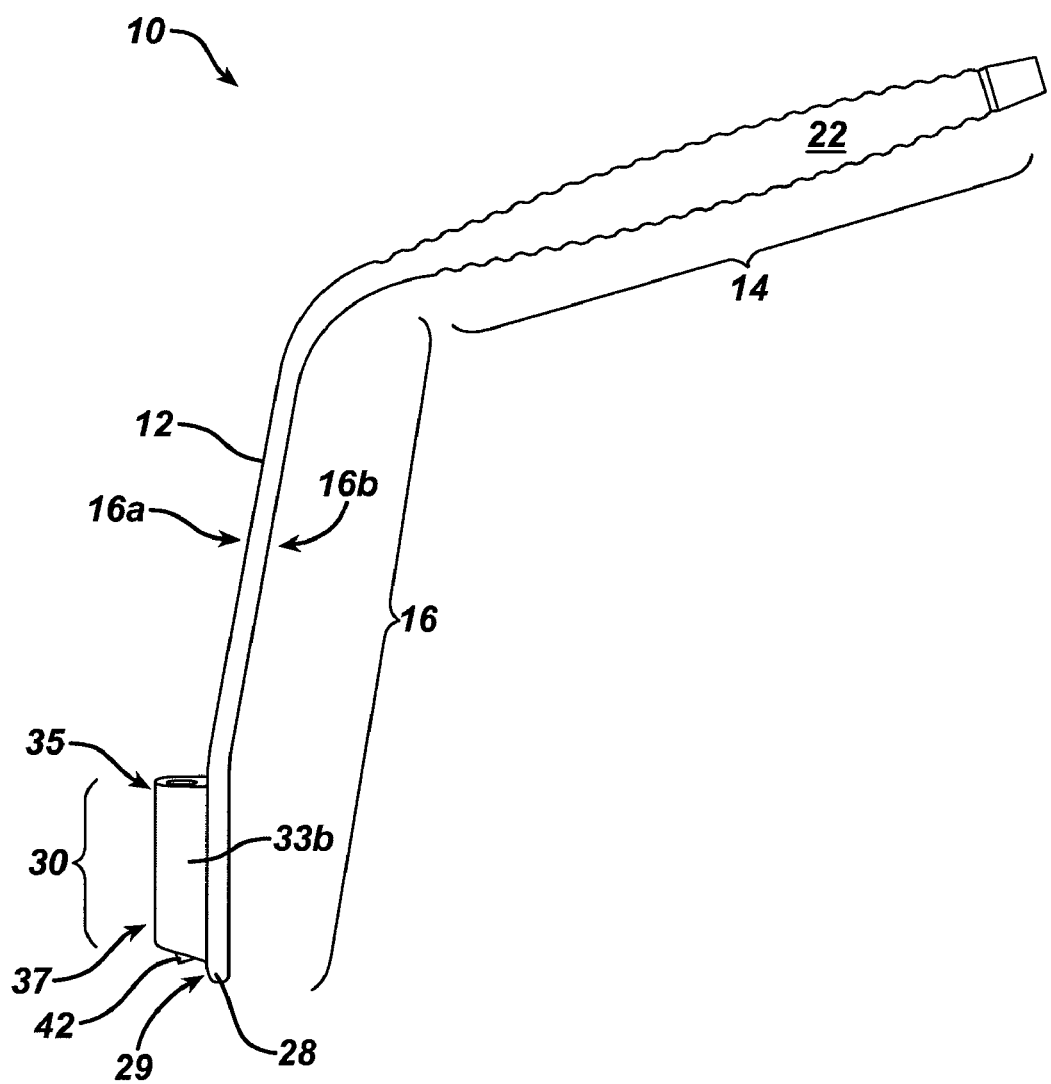
FIG. 2 is a side view of the device shown in FIG. 1.
Figure 3:
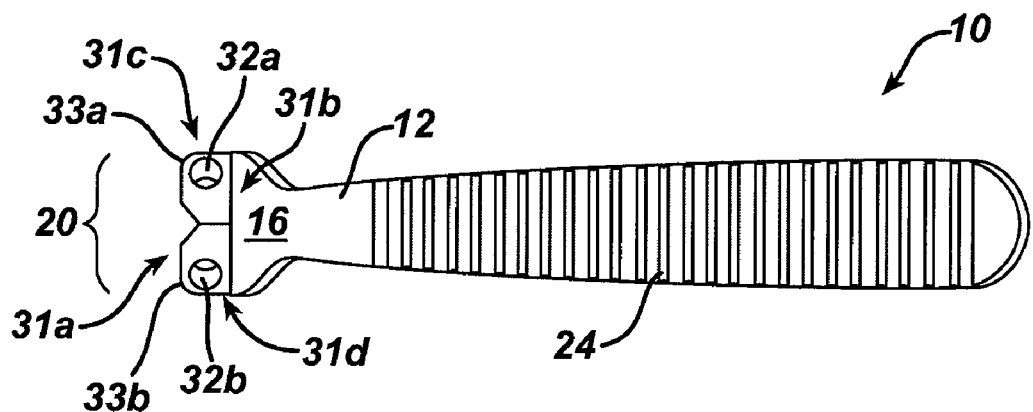
FIG. 3 is a top view of the device shown in FIG. 1.

The guide member 30, which is formed on, mated to, or integrally formed with the distal portion 16 of the elongate member 12, can also have a variety of configurations, but it should include at least one pathway formed therein for receiving a tool, such as, for example, an awl, a drill bit, a fastener, or a driver device. The pathway(s) is preferably effective to guide the tool to a spinal implant coupled thereto. In the embodiment illustrated in FIGS. 1-4, the guide member 30 includes two pathways 32a, 32b in the form of lumens extending therethrough. The lumens 32a, 32b can be defined by or formed in two barrels and/or alternatively the lumens 32a, 32b can be formed in a housing. As shown in FIGS. 1-4, the lumens 32a, 32b extend through first and second barrels 33a, 33b that are mated to one another to form a substantially rectangular housing. The housing 30 generally includes opposed front and back sidewalls 31a, 31b, opposed lateral sidewalls 31c, 31d extending between the front and back sidewalls 31a, 31b, and proximal and distal ends 35, 37, as shown in FIGS. 2 and 3. The lumens 32a, 32b extend therethrough between the proximal and distal ends 35, 37 thereof.

Figure 4:
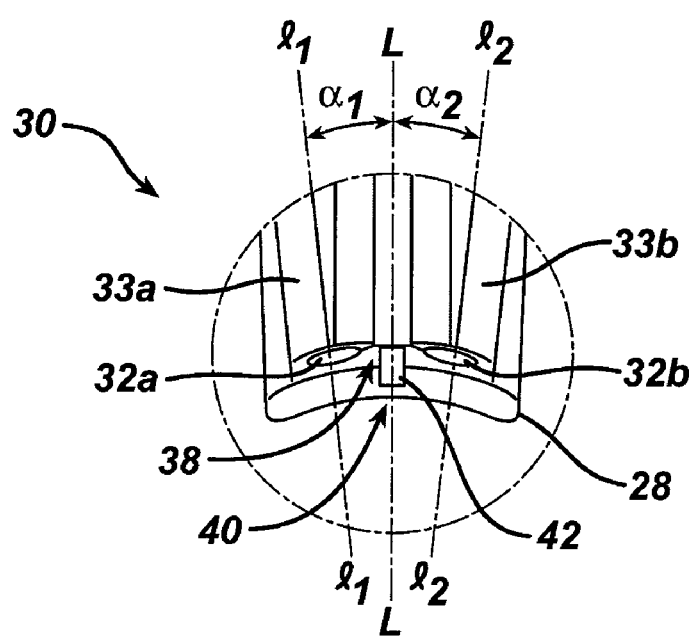
FIG. 4 is an enlarged view of the distal portion of the device shown in FIG. 1.

Each lumen 32a, 32b in the guide member 30 can be positioned at an angle with respect to one another, as shown in FIG. 4. More particularly, the longitudinal axes $l_1$, $l_2$ of each barrel 33a, 33b can be positioned at an angle $\alpha_1$, $\alpha_2$ with respect to a longitudinal axis L of the elongate member 12, such that the barrels 33a, 33b extend away from one another in a distal-to-proximal direction. The angles $\alpha_1$, $\alpha_2$ are determinative of the entry angle of a tool or device being inserted through the lumens 32a, 32b in each barrel 33a, 33b, and thus the angles $\alpha_1$, $\alpha_2$ should be set based on the intended use. The angles $\alpha_1$, $\alpha_2$ of one or both barrels 33a, 33b can optionally be adjustable. While the angles $\alpha_1$, $\alpha_2$ of the barrels 33a, 33b can vary, the barrels 33a, 33b preferably lie in a plane that is substantially parallel to at least a portion of a front surface 16a of the distal portion 16 of the elongate member 12. This is particularly advantageous in that it only requires a relatively small incision to be made in order to introduce the instrument into the surgical site, as the parallel guide member 30 reduces the size of the instrument compared to a device in which the guide member 30 is positioned at an angle with respect to the elongate member 12.

While not shown, the barrels 33a, 33b can be removably or fixedly mated to one another and/or to the guide member 30. For example, a base plate (not shown) can extend between the distal end 37 of each barrel 33a, 33b to mate the barrels 33a, 33b to one another and/or to the guide member 30. The base plate can include bores formed therein for removably or fixedly receiving the barrels 33a, 33b. Removable barrels 33a, 33b are particularly advantageous in that they allow barrels having different lengths to be selected based on the intended use.

Figure 5A:
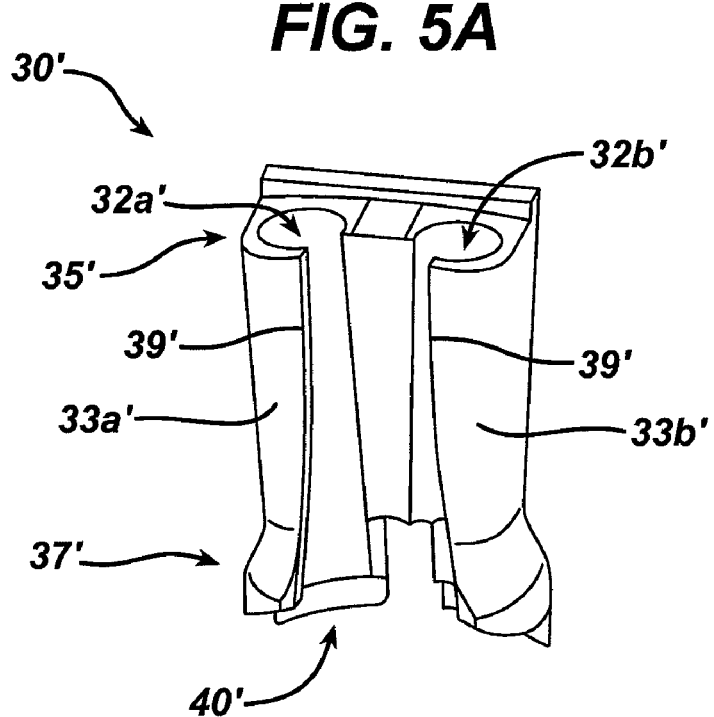
FIG. 5A is an enlarged, front view of another embodiment of a guide member for use with a device in accordance with the present invention.
Figure 5B:
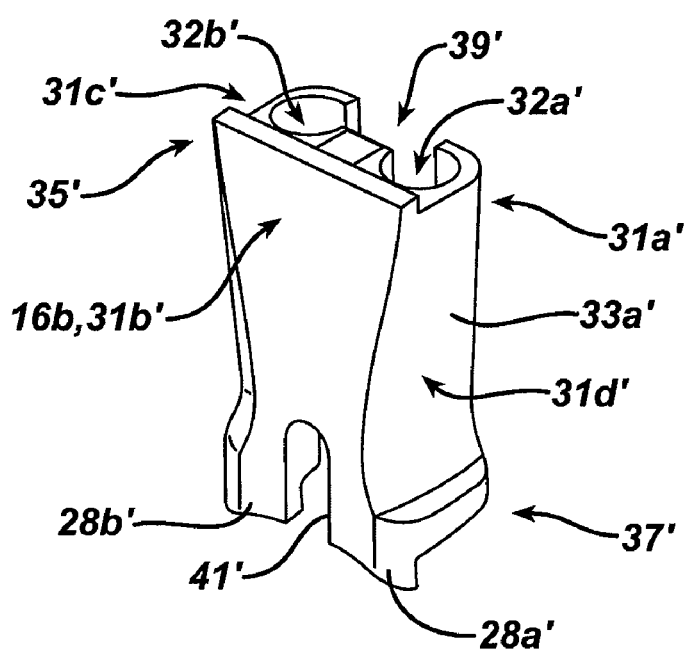
FIG. 5B is an enlarged, back view of the guide member shown in FIG. 5A.

FIGS. 5A and 5B illustrate another embodiment of a guide member 30' for use with the tissue retractor and guide device in accordance with the present invention. As shown, guide device 10' is similar to guide device 10, however the guide member 30' is in the form of a substantially hollow housing having first and second pathways 32a', 32b' formed therein and extending therethrough between proximal and distal ends 35', 37' thereof. The housing 30' includes opposed front and back sidewalls 31a', 31b', and opposed lateral sidewalls 31c', 31d' extending between the front and back sidewalls 31a', 31b'. The proximal end 35' of the back sidewall 31b' is preferably mated to the distal portion 16' of the elongate member 12', and more preferably the distal portion 12b' of the elongate member 12' is positioned at an angle with respect to the back sidewall 31b' of the guide member 30'. The back sidewall 31b' and the elongate member 12' can, however, optionally be integrally formed with one another, or mated to one another, at any other location and in any configuration.

The pathways 32a', 32b' in guide member 30' extend through the housing 30' and they are defined by the lateral sidewalls 31c', 31d' of the housing 30', in combination with the back sidewall 31b'. In an exemplary embodiment, each lateral sidewall 31c', 31d' has a substantially semi-cylindrical shape or is C-shaped. Accordingly, the sidewalls 33a', 33b' are substantially similar to barrels 33a, 33b, however, rather than having cylindrical lumens extending therethrough, they are at least partially open as a result of a cut-out portion 39' that extends therebetween, as will be discussed in more detail below. Each pathway 32a', 32b' is still configured to receive and guide a tool toward a spinal fixation plate coupled to the guide member 21'.

A person skilled in the art will appreciate that the guide member, and each pathway formed within the guide member, can have a variety of other shapes, sizes, and configurations as long as the pathway(s) is effective to guide a tool to a spinal implant.

Referring back to FIGS. 1-4, in another embodiment of the present invention, the guide member 30 can be adapted to rest against a spinal implant, such as a spinal fixation plate, and more particularly the guide member 30 can include a distal end surface 37 having a shape that is adapted to match the contour of a spinal fixation plate. By way of non-limiting example, as shown in FIGS. 1 and 4, the distal end 37 of the housing 30, i.e., barrels 33a, 33b, can have a substantially concave shape that is adapted to rest against a spinal fixation plate having a convex surface. The shape should, however, result in the alignment of the pathways in the guide member, i.e., lumens 32a, 32b in barrels 33a, 33b, with corresponding bores formed in a spinal fixation plate, as will be discussed below.

The device 10 can also other include features to facilitate placement of the device 10 at a surgical site, and more particularly that are adapted to align the guide member 30 with a spinal implant and/or prevent rotation between the guide member 30 and a spinal implant. In the embodiment illustrated in FIGS. 1-2 and 4, the elongate member 12 can include an extension portion 28 that is adapted to be positioned adjacent to a perimeter or edge of a spinal implant to provide a rough alignment between the device 10 and the spinal implant. The extension portion 28 can be formed on a distal end 12b of the elongate member 12 and/or it can be formed on the guide member 30. It should, however, extend distally beyond the distal-most end of the guide member 30 to allow the extension portion 28 to rest against an edge of the implant while the guide member 30 is juxtapositioned on a surface of the implant. As shown in FIGS. 1-2 and 4, the guide member 30 is attached to the distal portion 16 of the elongate member 12 at a position that is just proximal to the distal-most end 38 of the guide member 30, such that the distal-most portion of the elongate member 12 forms the extension portion 28.

In use, the front surface of extension portion 28 can abut the perimeter or edge of a spinal plate 80 to align the guide member 30 with the plate 70. Accordingly, the front surface 29 of the extension portion 28 should have a shape that matches the contour of at least a portion of the perimeter of an implant used therewith. In an exemplary embodiment, the front surface 29 of the extension portion 28 is substantially planar to rest against a planar surface on a spinal implant. In other embodiments, however, the front surface 29 of the extension portion 28 can have a concave surface that is adapted to match the contour of an opposed convex surface on the spinal plate, thereby further aligning the device 10 with respect to the plate 80. The extension portion 28 can also include a distal-most end 40 that is adapted to rest against a vertebral body, and more preferably the distal-most end 40 can have a substantially concave shape to match the contour of a vertebra. A person skilled in the art will appreciate that the distal-most end 40 can have a variety of configurations, shapes and sizes, and it can be adapted to rest against a vertebra and/or against a spinal fixation plate.

FIGS. 5A-5B illustrate another embodiment of an extension portion formed on guide member 30'. As shown, the guide member 30' includes two tabs 28a', 28b' that extend distally from the back sidewall 16b', 31b', and at least partially from the lateral sidewalls 31c', 31d', of the guide member 30'. The tabs 28a', 28b' each preferably have a substantially concave inner surface, as shown in FIG. 5A, such that they match the contour of a substantially concave outer surface formed around opposed screw bores formed in a spinal fixation plate. This allows the tabs 28a', 28b' to rest against the perimeter or edge of the spinal fixation plate. The tabs 28a', 28b' can also optionally be adapted to provide an interference fit with outer edges of the spinal fixation plate to engage the spinal fixation plate. By way of non-limiting example, the tabs can be formed on the opposed lateral sidewalls 31c', 31d' such that they can engage an implant therebetween. The tabs can also optionally be flexible or include other features to facilitate engagement of a spinal implant.

In another embodiment of the present invention, the tissue retractor and guide device can include one or more mating elements formed on a portion thereof to at least temporarily mate the device to a spinal implant, such as a spinal fixation plate. By way of non-limiting example, FIG. 4 illustrates one embodiment of a mating element in the form of a protrusion or pin member 42 that extends from a distal surface 38 of the guide member 30 at a location that is substantially between the first and second barrels 33a, 33b. The pin member 42 is adapted to extend into corresponding detents or bores formed in a spinal fixation plate, such as, for example, spinal plate 80 show in FIG. 6. The pin member 42 can optionally extend at an angle to further facilitate grasping the spinal plate 80. In an exemplary embodiment, the mating element 42 is adapted to prevent rotation between the guide member 30 and the spinal plate 80 to provide stability to the connection. By way of non-limiting example, mating elements with non-symmetrical shapes, such as a pin with a non-circular cross section (e.g. rectangular, oval, triangular, irregular), a multi-pronged mating element, or a tongue and groove combination, can prevent or reduce the tendency of the device 10 to pivot with respect to the spinal plate 80.

A person skilled in the art will appreciate that a variety of techniques can be used to mate the device 10 to the spinal plate 80, and that the mating element 42 can be formed on any portion of the device 10 and it can be adapted to grasp any portion of the spinal plate 80. By way of non-limiting example, other suitable mating techniques include a snap-fit engagement, an interference fit, a spring clip, a threaded engagement, and any other mechanical connection.

In other embodiments of the present invention, the guide member 30, 30' can include one or more cut-out portions or windows formed therein to facilitate visual access to a spinal fixation plate coupled thereto. The cut-out portions can be formed anywhere in the housing 30, 30', but in an exemplary embodiment, as shown in FIG. 5A, a cut-out portion 39' is formed in a front sidewall 31b' of the housing 21' between the first and second pathways 32a', 32b', and it extends between the proximal end 35' and distal end 37' of the housing 30'. As a result, the pathways 32a', 32b' are separated by the cut-out portion 39'. As previously mentioned, the cut-out portion 29' is particularly advantageous in that it provides the surgeon with improved visual access to a spinal plate attached to the guide member 30', as well as to the tools and devices used in connection with the guide member 30' and spinal fixation plate.

The guide member 30, 30' can also optionally include a second, distal cut-out portion, such as cut-out portion 41' shown in FIG. 5B, that is formed adjacent to the distal end 37' of the housing 30'. This cut-out portion 41' avoids interference by the guide member 30' with a temporary fixation pin that is disposed through the spinal fixation plate to temporarily attach the plate to bone. Since temporary fixation pins are typically only placed on opposed ends of the plate, the distal cut-out portion 41' is preferably only formed on a back side 31a' of the guide member 21', 23'.

Figure 6:
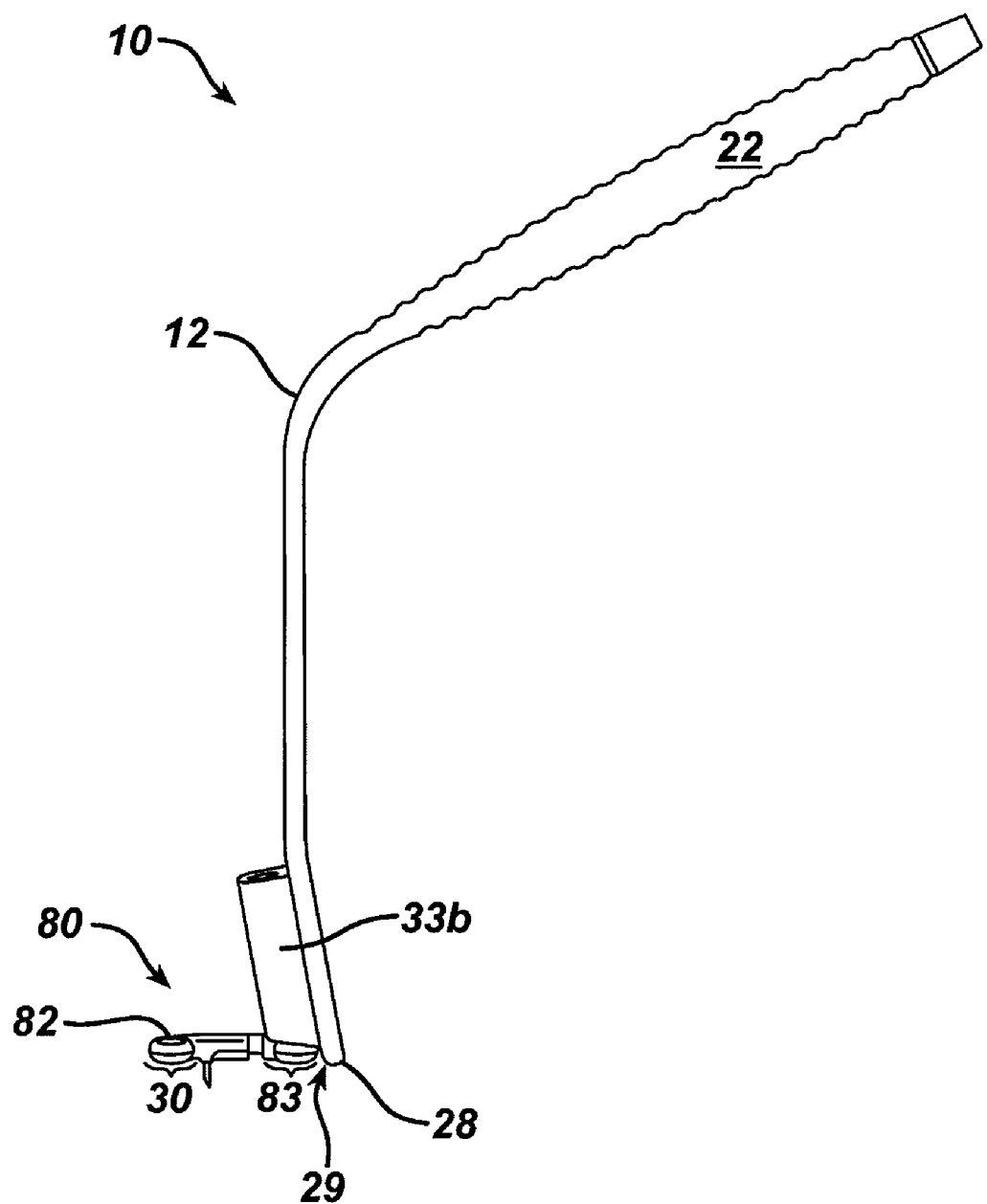
FIG. 6 is a side view of the tissue retractor and guide device of FIG. 1 mated to one embodiment of a spinal fixation plate.
Figure 7:
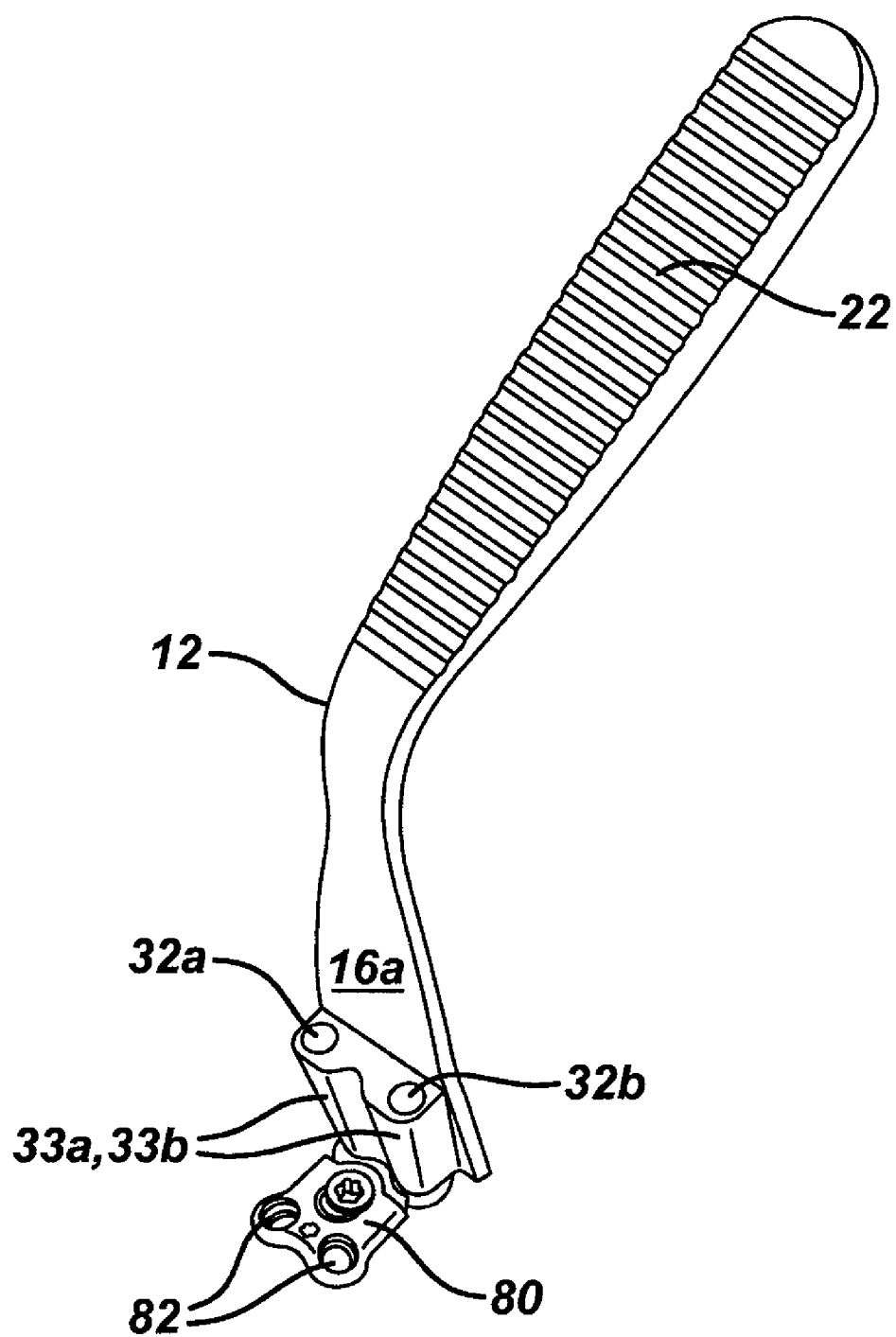
FIG. 7 is a perspective view of the device and the fixation plate shown in FIG. 6.

In use, the device 10, 10' is adapted to be juxtapositioned on a spinal fixation plate. Accordingly, by way of non-limiting example, FIGS. 6 and 7 illustrate device 10 mated to an exemplary embodiment of a spinal fixation plate 80. In general, the spinal plate 80 includes a superior and an inferior portion 81, 83, each having at least one bore 82 formed therein for receiving a fixation device, e.g., a screw, to mate the plate 80 to a vertebra. The inferior and superior portions 81, 83 can optionally be slidably movable with respect to one another such that the height of the plate 80 is adjustable. In use, the plate 80 is adapted to span across two vertebra such that the proximal portion 81 is mated to one vertebra and the distal portion 83 is mated to an adjacent vertebra. As indicated above, the device 10 can be mated to one of the inferior or superior portions 81, 83 of the spinal plate 80 by first positioning the extension portion 28 adjacent to a side on one of the inferior and superior portions 81, 83 of the spinal plate 80 to provide a rough alignment. The handle 22 on the elongate member can then be manipulated to insert the mating element, e.g., pin 42, on the guide member 30 into the corresponding receiving-bore (not shown) formed in the spinal plate 80. In this configuration, the lumens 32a, 32b of guide member 30 are aligned with the bores 82 formed in the spinal plate 80.

With the distal portion of device 10 mated to and aligned with the spinal plate 80, the handle 22 can be used to retract tissue around the implant site, and to position the plate against adjacent vertebrae. The handle can then either be held in position, or attached to an external support structure, such as a Bookwalter, using a clamp disposed on the handle or on the external support, to maintain the position of the spinal plate against the vertebrae.

When the plate is properly positioned against the spine and the tissue retractor and guide device 10 is aligned with the plate, a tool, such as a drill, awl, tap, or implant, can be passed through the each lumen 32a, 32b in the guide member 30 to form a borehole in the vertebrae and/or to insert a spinal implant into the vertebrae.

Figure 8:
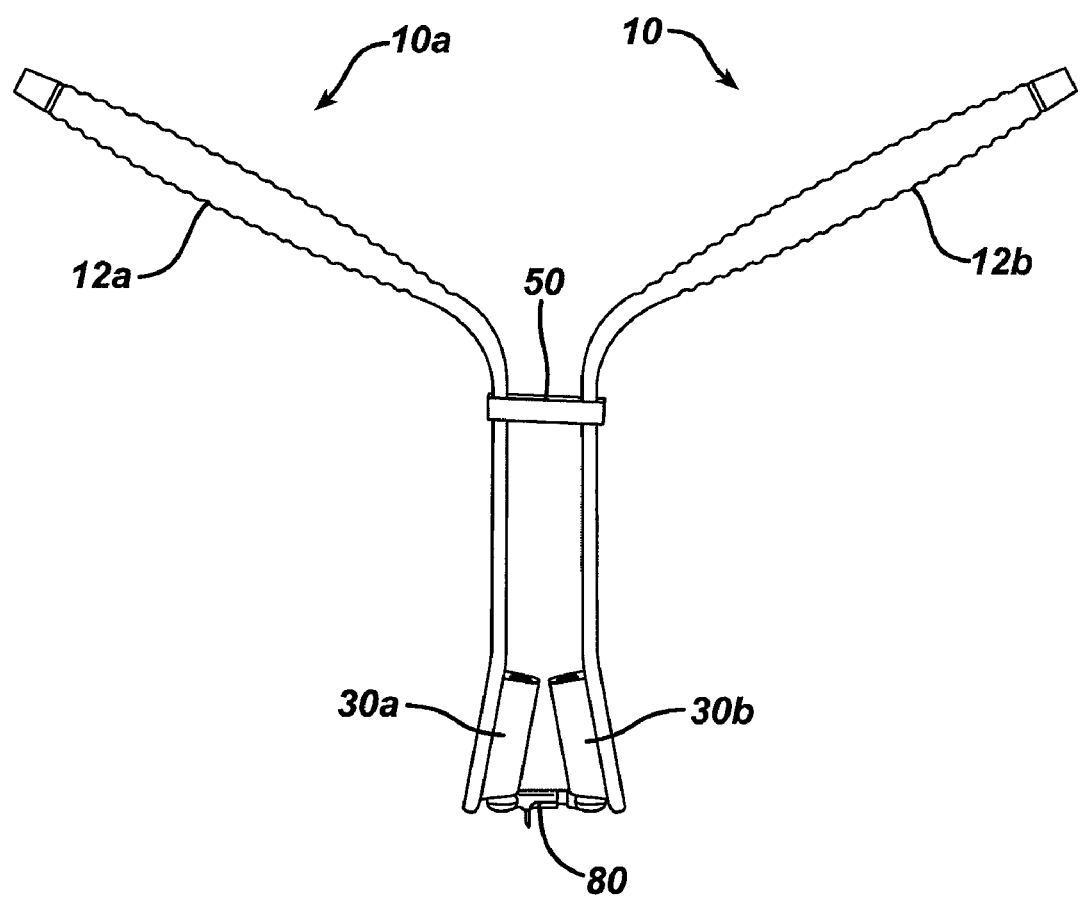
FIG. 8 is a side view of two tissue retractor and guide devices mated to one another by a cross member, and mated to a spinal fixation plate according to another embodiment of the present invention.

In another embodiment, as shown in FIG. 8, two tissue retractor and guide devices can be mated to a single spinal plate 80 to retract tissue disposed around the entire plate 80, and to allow a surgeon to efficiently prepare the vertebrae and implant the plate 80. As shown, a first tissue retractor and guide device 10a is mated to a inferior portion 81 of the spinal plate 80, and a second tissue retractor and guide device 10b is mated to the superior portion 83 of the spinal plate 80. Where the plate 80 has an adjustable height, as previously discussed, the guide devices 10a, 10b are preferably used to fully extend the plate 80. In order to maintain the position of the two devices 10a, 10b with respect to one another, the present invention also provides a cross member 50 that is removably matable to the two devices 10a, 10b. In an exemplary embodiment, two tissue retractor and guide devices 10a, 10b and a cross member 50 are provided in a kit.

The cross member 50 can have a variety of configurations, and in one embodiment (not shown), it can include an elongate rod having opposed ends. Each end is preferably adapted to removably mate to a tissue retractor and guide device 10a, 10b. In another embodiment, as shown in FIG. 7 the cross member 50 is in the form of a substantially rectangular-shaped housing that is adapted to fit around the elongate member 12a, 12b of each device 10a, 10b. The rectangular shape of the cross member 50 is particularly advantageous in that it provides a window to the surgical site, thereby allowing the surgeon to access the guide member 30a, 30b on each device 10a, 10b. A person skilled in the art will appreciate that the cross member 50 can have virtually any shape and size including, but not limited to, oval, rectangular, circular, and irregular.

The device can be formed from a variety of materials, including metals, such as stainless steel, and plastics. In an exemplary embodiment, however, the device, or at least a portion of the device, is formed from a radio lucent material to facilitate intraoperative imaging of the surgical site. By way of non-limiting example, suitable radio lucent materials include carbon fiber, radel, or any other biocompatible plastic or other material.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A tissue retractor and guide device, comprising:
an elongate member having proximal and distal portions, the distal portion including a surface adapted to retract tissue; and
a guide member coupled to the distal portion of the elongate member and having first and second pathways extending therethrough for receiving a tool, the pathways having central longitudinal axes that are substantially parallel to at least a portion of a front surface of the distal portion of the elongate member, and having a cut-out portion extending between the first and second pathways, the guide member being adapted to be positioned in relation to a spinal implant such that each of the pathways in the guide member is aligned with at least one corresponding bore formed in the spinal implant to guide a tool through the bore and the cut-out portion provides visual access to the spinal implant.

2. The device of claim 1, wherein the guide member has a width that is equal to or less than a width of at least a portion of the distal portion of the elongate member such that the distal portion of the elongate member is effective to retract tissue disposed adjacent to the guide member.

3. The device of claim 1, wherein the guide member is adapted to be juxtapositioned on the spinal implant.

4. The device of claim 1, wherein the surface on the distal portion of the elongate member is substantially planar.

5. The device of claim 1, wherein the guide member includes front and back opposed sidewalls, and opposed lateral sidewalls extending between the front and back sidewalls, the back sidewall of the guide member being coupled to the elongate member.

6. The device of claim 5, wherein the distal portion of the elongate member is positioned at an angle with respect to the back sidewall of the guide member.

7. The device of claim 5, wherein the opposed lateral sidewalls of the guide member are substantially C-shaped.

8. The device of claim 5, further comprising at least one extension portion extending distally from the guide member and adapted to align the first and second pathways in the guide member with corresponding bores formed in a spinal implant.

9. The device of claim 8, wherein the at least one extension portion comprises first and second tabs extending from the opposed lateral sidewalls of the guide member.

10. The device of claim 9, wherein each tab has a substantially concave inner surface that is adapted to be positioned against a substantially concave outer surface formed on a perimeter of a spinal implant.

11. The device of claim 8, wherein the at least one extension portion extends distally from the back sidewall of the guide member.

12. The device of claim 11, wherein the at least one extension portion is formed on the distal portion of the elongate member and it extends a distance beyond a distal-most end of the guide member.

13. The device of claim 11, wherein a distal-most surface of the extension portion is substantially concave to match the contour of a vertebral body.

14. The device of claim 1, wherein the pathways are positioned at an angle with respect to one another.

15. The device of claim 1, wherein the cut-out portion is formed in a front sidewall of the guide member between the two pathways.

16. The device of claim 15, wherein the cut-out portion extends from the proximal end to the distal end of the guide member.

17. The device of claim 1, wherein the proximal portion of the elongate member is positioned at an angle with respect to the distal portion of the elongate member.

18. The device of claim 17, wherein the angle is in the range of about 110° to 160°.

19. The device of claim 1, wherein the proximal portion of the guide member includes a clamp member adapted to mate to an external support.

20. The device of claim 1, wherein the proximal portion of the guide member includes a post adapted to attach to a clamp member on an external support.

21. A tissue retractor and guide device, comprising:
an elongate member having a proximal portion and a distal portion that is adapted to retract tissue; and
a guide member coupled to the distal portion of the elongate member and adapted to be juxtapositioned on a spinal implant, the guide member including at least one pathway extending therethrough for receiving a tool, and at least one cut-out portion in a front sidewall of the guide member adapted to provide visual access to the spinal implant, the at least one cut-out portion extending from a proximal end of the guide member to a distal end of the guide member, and the at least one pathway having a central longitudinal axis that extends in a proximal-distal direction and that is substantially parallel to a plane containing the front sidewall of the guide member, the plane of the front sidewall extending in a proximal-distal direction.

22. The device of claim 21, wherein the guide member includes front and back opposed sidewalls, and opposed lateral sidewalls extending between the front and back sidewalls, the back sidewall of the guide member being coupled to the elongate member.

23. The device of claim 22, wherein the guide member includes two pathways extending therethrough.

24. The device of claim 23, wherein the cut-out portion is formed in the front sidewall between the two pathways.

25. The device of claim 22, wherein the opposed lateral sidewalls of the guide member are substantially C-shaped.

26. A tissue retractor and guide kit, comprising:
first and second tissue retractor and guide devices adapted to couple to a spinal implant, the first and second devices having
a guide member having opposed front and back sidewalls, opposed lateral sidewalls extending between the front and back sidewalls, and first and second pathways formed therein for receiving a tool, and
an elongate member having a proximal, handle portion, and a distal, tissue-retracting portion coupled to the back sidewall of the guide member; and
a cross member removably and reattachably connected to the first and second tissue retractor and guide devices.

27. The kit of claim 26, wherein the cross member comprises a substantially rectangular housing.

28. The kit of claim 26, wherein the cross member comprises an elongate rod having opposed ends, each end being adapted to removably mate to a tissue retractor and guide device.

29. A spinal fixation kit, comprising:
a spinal fixation plate having
a superior portion with at least one bore formed therein for receiving a fixation device effective to mate the superior portion to a first vertebra, and
an inferior portion with at least one bore formed therein for receiving a fixation device effective to mate the inferior portion to a second, adjacent vertebra; and
at least one tissue retractor and guide device adapted to be juxtapositioned on the spinal fixation plate, the at least one tissue retractor and guide device having
a guide member having opposed front and back sidewalls, opposed lateral sidewalls extending between the front and back sidewalls, and first and second pathways formed therein for receiving a tool, at least a portion of the first and second pathways being in communication with one another, and
an elongate member having a proximal, handle portion, and a distal, tissue-retracting portion coupled to the back sidewall of the guide member;
wherein the first and second pathways have central longitudinal axes that extend substantially parallel to at least a portion of the distal, tissue-retracting portion of the elongate member and that do not intersect any portion of the elongate member, and wherein at least one of the first and second pathways in the guide member is aligned with a bore formed in the spinal fixation plate when the guide member is juxtapositioned on the spinal fixation plate.

30. The kit of claim 29, wherein the first and second pathways are adapted to be aligned with two adjacent bores formed in at least one of the superior portion and the inferior portion of the spinal fixation plate.

31. The kit of claim 30, wherein the pathways are positioned at an angle with respect to one another.

32. The kit of claim 30, further comprising at least one cut-out portion formed in the guide member and adapted to provide visual access to a spinal implant coupled thereto.

33. The kit of claim 30, further comprising first and second tabs extending distally from a distal-most end of the guide member, the tabs being adapted to align the pathways in the guide member with bores formed in the spinal fixation plate.

34. The kit of claim 33, wherein the first and second tabs extend from the back sidewall of the guide member.

35. The kit of claim 33, wherein each tab has a substantially concave inner surface that is adapted to be positioned against a substantially concave outer surface formed on a perimeter of a spinal fixation plate.

36. The kit of claim 33, wherein a distal-most surface of each tab is substantially concave to match the contour of a vertebral body.

37. The kit of claim 29, wherein the guide member includes a cut-out portion formed in the front sidewall between the first and second pathways.

38. The kit of claim 37, wherein the cut-out portion extends between the proximal and distal ends of the guide member.

39. The kit of claim 37, wherein the opposed lateral sidewalls of the guide member are substantially C-shaped.

40. The kit of claim 29, wherein a distal-most end of the elongate member extends a distance beyond a distal-most end of the guide member to form an extension portion, the extension portion being adapted to rest against a perimeter of the spinal fixation plate to align the guide member with the spinal fixation plate.

41. The kit of claim 29, wherein a distal end of the guide member has at least one mating element formed thereon and adapted to mate with a corresponding mating element formed on the spinal fixation plate.

42. The kit of claim 41, wherein the at least one mating element has a shape that is adapted to prevent rotation of the guide member with respect to the spinal fixation plate when the guide member is positioned on the spinal fixation plate.

43. The kit of claim 29, wherein the superior and inferior portions of the spinal fixation plate are slidably movable with respect to each other between a retracted position and an extended position.

44. The kit of claim 43, further comprising a cross member effective to mate two tissue retractor guide devices to one another, and to maintain the spinal fixation plate in the extended position when the devices are mated to the superior and inferior portions of the spinal fixation plate.

* * * * *

UNITED STATES PATENT AND TRADEMARK OFFICE
CERTIFICATE OF CORRECTION

| | |
|---|---|
| PATENT NO. | : 7,909,848 B2 |
| APPLICATION NO. | : 10/777019 |
| DATED | : March 22, 2011 |
| INVENTOR(S) | : Patel et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1146 days.

Signed and Sealed this
Ninth Day of August, 2011

David J. Kappos
*Director of the United States Patent and Trademark Office*